United States Patent
Ando

(10) Patent No.: US 9,072,666 B2
(45) Date of Patent: Jul. 7, 2015

(54) METHOD FOR PRODUCING ORGANOPOLYSILOXANE EMULSION COMPOSITION

(71) Applicant: Shin-Etsu Chemical Co., Ltd., Chiyoda-ku (JP)

(72) Inventor: Yuji Ando, Annaka (JP)

(73) Assignee: Shin-Etsu Chemical Co., Ltd., Chiyoda-ku (JP)

( * ) Notice: Subject to any disclaimer, the term of this patent is extended or adjusted under 35 U.S.C. 154(b) by 0 days.

(21) Appl. No.: 14/347,152

(22) PCT Filed: Jan. 24, 2013

(86) PCT No.: PCT/JP2013/051484
§ 371 (c)(1),
(2) Date: Mar. 25, 2014

(87) PCT Pub. No.: WO2013/153833
PCT Pub. Date: Oct. 17, 2013

(65) Prior Publication Data
US 2014/0378553 A1    Dec. 25, 2014

(30) Foreign Application Priority Data

Apr. 11, 2012 (JP) .................................. 2012-089871

(51) Int. Cl.
| | | |
|---|---|---|
| C08G 77/16 | (2006.01) |
| A61K 8/04 | (2006.01) |
| C08K 5/42 | (2006.01) |
| C08L 71/00 | (2006.01) |
| C08L 83/04 | (2006.01) |
| A61K 8/891 | (2006.01) |
| A61Q 5/02 | (2006.01) |
| C09D 183/06 | (2006.01) |

(52) U.S. Cl.
CPC ... *A61K 8/04* (2013.01); *C08K 5/42* (2013.01); *C08G 77/16* (2013.01); *C08L 71/00* (2013.01); *C08L 83/04* (2013.01); *A61K 8/891* (2013.01); *A61K 2800/21* (2013.01); *A61Q 5/02* (2013.01); *C09D 183/06* (2013.01)

(58) Field of Classification Search
CPC ........ C08G 77/16; C08K 5/42; C09D 183/06; C08L 71/00
USPC ............................................ 516/55; 524/837
See application file for complete search history.

(56) References Cited

U.S. PATENT DOCUMENTS

| | | | |
|---|---|---|---|
| 2,891,920 A | 6/1959 | Hyde et al. |
| 3,294,725 A | 12/1966 | Findlay et al. |
| 5,905,131 A | 5/1999 | Joseph et al. |
| 7,745,533 B2 | 6/2010 | Paul |
| 2007/0276087 A1 | 11/2007 | Paul |

FOREIGN PATENT DOCUMENTS

| | | | |
|---|---|---|---|
| CN | 101111534 A | | 1/2008 |
| JP | 34-2041 | | 4/1959 |
| JP | 41-13995 | | 8/1966 |
| JP | 04-178429 | * | 6/1992 |
| JP | 4-198321 | | 7/1992 |
| JP | 8-188744 | | 7/1996 |
| JP | 9-110992 | | 4/1997 |
| JP | 3145394 | | 3/2001 |
| JP | 2003-252994 | | 9/2003 |
| JP | 2003-252994 A | | 9/2003 |
| JP | 2008-528775 | | 7/2008 |
| WO | WO 2006/081978 A1 | | 8/2006 |
| WO | 2012 119916 | * | 9/2012 |

OTHER PUBLICATIONS

International Search Report issued Apr. 16, 2013, in PCT/JP13/051484 filed Jan. 24, 2013.
Combined Taiwanese Office Action and Search Report issued Mar. 19, 2014, in Taiwanese Patent Application No. 102103884 with English translation and English translation of category of cited documents.
Combined Chinese Office Action and Search Report issued Aug. 26, 2014 in Chinese Patent Application No. 201380002308.3 (with English language translation).
Extended European Search Report issued Dec. 1, 2014 in Patent Application No. 13774964.4.

* cited by examiner

*Primary Examiner* — Kuo-Liang Peng
(74) *Attorney, Agent, or Firm* — Oblon, McClelland, Maier & Neustadt, L.L.P.

(57) ABSTRACT

A method for producing an organopolysiloxane emulsion composition, which enables the organopolysiloxane to be formed with a high viscosity in a short period of time, and suppresses the amount of octamethylcyclotetrasiloxane (D4) to not more than 3,000 ppm. Specifically, a method for producing an organopolysiloxane emulsion which includes emulsifying a mixture containing an organopolysiloxane represented by formula: $HO(R^1_2SiO)_nH$ and having a D4 content of not more than 1,000 ppm, a nonionic surfactant, an anionic surfactant, and water, and subjecting the obtained emulsion composition to emulsion polymerization, thus preparing the emulsion composition.

5 Claims, No Drawings

METHOD FOR PRODUCING ORGANOPOLYSILOXANE EMULSION COMPOSITION

CROSS REFERENCE TO RELATED APPLICATION

This application is a 371 of PCT/JP2013/051484, filed on Jan. 24, 2013, and claims priority to Japanese Patent Application No. 2012-089871, on Apr. 11, 2012.

TECHNICAL FIELD

The present invention relates to a method for producing an organopolysiloxane emulsion composition that is useful in a variety of fields, including cosmetic materials, household items, and release agents.

BACKGROUND ART

A variety of fields, including the fields of cosmetic materials, household items, and release agents, require the formation of a high-viscosity organopolysiloxane as a fine emulsion. However, when a high-viscosity organopolysiloxane is subjected to direct emulsification, the limit for the particle size of the emulsion particles is about several microns, and obtaining a finer emulsion is difficult. As a result, a variety of investigations have been undertaken into methods of producing emulsions by emulsion polymerization, with the aim of obtaining fine emulsion particles.

For example, methods in which a cyclic siloxane oligomer is subjected to emulsion polymerization in an emulsified state using a strong acid or a strong base are already known (Patent Documents 1 and 2). By using these methods, emulsions can be obtained in which the particle size of the emulsion particles is 300 nm or less.

However, in recent years, concerns have been raised about the effects of octamethylcyclotetrasiloxane as an environmental impact substance, and products in which the octamethylcyclotetrasiloxane content has been suppressed are now being demanded. In the methods disclosed in Patent Documents 1 and 2, it is known that the organopolysiloxane contained within the obtained emulsion contains 40,000 ppm or more of octamethylcyclotetrasiloxane, and therefore methods of suppressing the amount of octamethylcyclotetrasiloxane produced are now being investigated.

For example, in one known method for producing an organopolysiloxane emulsion, an emulsion composed of (a) an organopolysiloxane represented by a general formula: HO(R$_2$SiO)$_m$H (wherein R represents identical or different monovalent hydrocarbon groups, and m represents a value corresponding with a viscosity at 25° C. within a range from 30 to less than 10,000 mm$^2$/s) and containing an amount of condensation-unreactive organosiloxane oligomers having 20 or fewer silicon atoms of not more than 5,000 ppm, (b) a polymerization catalyst (although in those cases where a surfactant having a catalytic action is used as the component (c), the component (b) is unnecessary), (c) a surfactant, and (d) water [in an amount of 30 to 1,000 parts by mass per 100 parts by mass of the component (a)] is subjected to an emulsion polymerization under conditions including a temperature of not more than 40° C. and a polymerization time of not more than 40 hours, and the amount of condensation-unreactive organosiloxane oligomers having 20 or fewer silicon atoms within the produced organopolysiloxane exceeds 1,000 ppm but is not more than 10,000 ppm (Patent Document 3). However, with this method, a problem arises in that even if the emulsion polymerization is conducted for 24 hours using an emulsification device such as a high-pressure Gaulin homogenizer, the viscosity of the organopolysiloxane in the emulsion is limited to 1,000,000 mm$^2$/s, and if the condensation time is lengthened in order to obtain a higher viscosity siloxane, then the amount of octamethylcyclotetrasiloxane exceeds 3,000 ppm.

As a result, being able to adjust the viscosity of the organopolysiloxane in the emulsion to a desired value using as short an emulsion polymerization time as possible is highly desirable, not only in terms of enhancing the production efficiency, but also from the viewpoint of suppressing the amount of octamethylcyclotetrasiloxane contained within the organopolysiloxane in the emulsion.

DOCUMENTS OF RELATED ART

Patent Documents

[Patent Document 1] JP Sho 34-2041 B
[Patent Document 2] JP Sho 41-13995 B
[Patent Document 3] JP 3,145,394 B

DISCLOSURE OF INVENTION

Problems to be Solved by the Invention

Accordingly, an object of the present invention is to provide a method for producing an organopolysiloxane emulsion composition, which enables the viscosity of the organopolysiloxane contained within the emulsion to be adjusted to a desired value in a shorter time than is conventionally possible, and in which the amount of octamethylcyclotetrasiloxane within the organopolysiloxane contained in the obtained emulsion is not more than 3,000 ppm.

Means to Solve the Problems

The inventors of the present invention discovered that by (1) using, as a raw material, an organopolysiloxane having a comparatively high molecular weight and having silanol groups at the molecular chain terminals, (2) using a nonionic surfactant and an anionic surfactant in a mass ratio within a range from 1:99 to 65:35 for the emulsification of the raw material organopolysiloxane, and (3) performing the initial stage of the emulsification in a small amount of water, the particle size of the emulsion particles in the obtained emulsion composition could be reduced to an extremely small value of 300 nm or less, the viscosity of the organopolysiloxane contained within the emulsion could be adjusted to the desired high viscosity in a shorter time than is conventionally possible, and the amount of octamethylcyclotetrasiloxane contained within the organopolysiloxane could be suppressed, and they were therefore able to complete the present invention.

In other words, a first aspect of the present invention provides a method for producing an organopolysiloxane emulsion composition, the method comprising:
(I) preparing a first emulsion composition by performing emulsification of a mixture comprising:
(A) 100 parts by mass of an organopolysiloxane represented by general formula (1) shown below, and having an octamethylcyclotetrasiloxane content of not more than 1,000 ppm, $$HO(R^1{}_2SiO)_nH \qquad (1)$$

wherein each $R^1$ independently represents a hydrogen atom or a substituted or unsubstituted hydrocarbon group of 1 to 20 carbon atoms, and n represents a number that yields a viscosity at 25° C. for the organopolysiloxane of 3,000 to 100,000 mm²/s, (B) 1 to 100 parts by mass of a nonionic surfactant, (C) 1 to 100 parts by mass of an anionic surfactant (provided that the mass ratio of component (B):component (C) is within a range from 1:99 to 65:35), and (D-1) 1 to 10 parts by mass of water, and (II) subjecting the first emulsion composition to emulsion polymerization, either without adding any water, or following the addition of (D-2) not more than 100,000 parts by mass of water, the emulsion polymerization performed at a temperature of less than 40° C., in the presence of an acid catalyst (E) (although this acid catalyst is unnecessary in those cases where the anionic surfactant (C) has a catalytic action), thus preparing the target emulsion composition, in which the viscosity at 25° C. of the organopolysiloxane generated in a polymerization time of not more than 15 hours is 300,000 mP·s or greater, and the amount of octamethylcyclotetrasiloxane contained in the organopolysiloxane is not more than 3,000 ppm.

A second aspect of the present invention provides an organopolysiloxane emulsion composition obtained using the method described above.

Effects of the Invention

According to the present invention, the desired emulsion composition can be obtained in a short period of time of not more than 15 hours. In other words, the average particle size of the emulsion particles in the obtained emulsion composition is an extremely fine value of 300 nm or less. The viscosity of the organopolysiloxane within the emulsion composition can be adjusted to a high viscosity exceeding 1,000,000 mPa·s, and in even in such cases, the amount of octamethylcyclotetrasiloxane contained in the organopolysiloxane is not more than 3,000 ppm.

EMBODIMENTS FOR CARRYING OUT THE INVENTION

—Materials—

The raw materials and materials used in the production method of the present invention are described below.

<(A) Organopolysiloxane>

The component (A) is an organopolysiloxane represented by general formula (1) shown below, and having an octamethylcyclotetrasiloxane content of not more than 1,000 ppm.

$$HO(R^1{}_2SiO)_nH \qquad (1)$$

In general formula (1), $R^1$ represents a hydrogen atom or a substituted or unsubstituted hydrocarbon group of 1 to 20 carbon atoms. Examples of the unsubstituted hydrocarbon group of 1 to 20 carbon atoms include alkyl groups of 1 to 20 carbon atoms, cycloalkyl groups of 3 to 20 carbon atoms, alkenyl groups of 2 to 20 carbon atoms, aryl groups of 6 to 20 carbon atoms, and aralkyl groups of 7 to 20 carbon atoms. Specific examples include alkyl groups such as a methyl group, ethyl group, propyl group, butyl group, pentyl group, hexyl group, heptyl group, octyl group, nonyl group, decyl group, dodecyl group, tetradecyl group, hexadecyl group and octadecyl group, cycloalkyl groups such as a cyclopentyl group and cyclohexyl group, alkenyl groups such as a vinyl group and allyl group, and aryl groups such as a phenyl group, tolyl group and naphthyl group. Examples of the substituted hydrocarbon group of 1 to 20 carbon atoms include the monovalent hydrocarbon groups of 1 to 20 carbon atoms mentioned above in which a portion of the hydrogen atoms have each been substituted with a halogen atom, amino group, acryloyloxy group, methacryloyloxy group, epoxy group, mercapto group, carboxyl group or hydroxyl group or the like. A hydrocarbon group of 1 to 6 carbon atoms is preferable, and specific examples include a methyl group, ethyl group, propyl group, butyl group and phenyl group. It is particularly preferable that at least 80% of all the $R^1$ groups are methyl groups.

In general formula (1), n represents a number that yields a viscosity at 25° C. for the organopolysiloxane of 3,000 to 100,000 mm²/s. If the viscosity is less than 3,000 mm²/s, then achieving the desired viscosity for the organopolysiloxane contained within the target emulsion requires a lengthening of the emulsion polymerization time, and the amount of octamethylcyclotetrasiloxane generated as a by-product during the emulsion polymerization tends to increase. In contrast, if the viscosity is too high, then the stability of the obtained target emulsion tends to worsen. Accordingly, the viscosity is preferably within a range from 3,000 to 50,000 mm²/s, and particularly preferably from 4,000 to 20,000 mm2/s.

The octamethylcyclotetrasiloxane content within the organopolysiloxane is not more than 1,000 ppm. If this amount exceeds 1,000 ppm, then there is a concern that, following the emulsion polymerization, when the viscosity of the organopolysiloxane reaches 300,000 mPa·s or more, the amount of octamethylcyclotetrasiloxane contained within the organopolysiloxane may exceed 3,000 ppm, which is undesirable. In order to produce an organopolysiloxane having an octamethylcyclotetrasiloxane content of 1,000 ppm or less, a distillation under reduced pressure, thin-film distillation or molecular distillation or the like may be performed.

<(B) Nonionic Surfactant>

Examples of the nonionic surfactant for the component (B) include polyoxyalkylene alkyl ethers, polyoxyalkylene alkylphenol ethers, polyoxyalkylene alkyl esters, polyoxyalkylene sorbitan alkyl esters, polyethylene glycol, polypropylene glycol and diethylene glycol. Among these, compounds represented by the general founula shown below are preferable:

$$R^2O(EO)_n(PO)_mH$$

wherein $R^2$ represents a linear or branched alkyl group of 8 to 30 carbon atoms, EO represents an ethylene oxide group, PO represents a propylene oxide group, the arrangement of EO and PO may be in blocks or random, and each of n and m independently represents an integer of 0 to 100, provided that n+m>0.

Compounds in which $R^2$ represents a linear or branched alkyl group of 8 to 12 carbon atoms, and each of n and m independently represents an integer of 0 to 25 are particularly preferable.

The amount used of this component is typically within a range from 1 to 100 parts by mass, preferably from 2 to 25 parts by mass, and particularly preferably from 3 to 10 parts by mass, per 100 parts by mass of the component (A). A single type of the component (B) may be used alone, or a combination of 2 or more types may be used.

<(C) Anionic Surfactant>

Examples of the anionic surfactant of the component (C) include:

alkylsulfuric acids or salts thereof represented by general formula (C-1):

$$R^3OSO_3M \qquad (C\text{-}1)$$

wherein $R^3$ represents a linear or branched alkyl group of 6 to 30 carbon atoms, M represents a hydrogen atom, an alkali metal atom such as potassium or sodium, an alkaline earth metal atom such as magnesium or calcium, an ammonium ion, or a quaternary ammonium ion, and alkylbenzenesulfonic acids or salts thereof represented by general formula (C-2):

$$R^3\text{—Ph-SO}_3M \quad\quad\quad (C\text{-}2)$$

wherein $R^3$ and M are as defined above in formula (C-1).

In formula (C-1) and formula (C-2), it is preferable that $R^3$ represents a linear or branched alkyl group of 6 to 12 carbon atoms, and M represents a hydrogen atom, an alkali metal atom such as potassium or sodium, an alkaline earth metal atom such as magnesium or calcium, an ammonium ion, or a quaternary ammonium ion.

Specific examples of the alkylsulfuric acid or salt thereof represented by formula (C-1) include hexylsulfuric acid, octylsulfiric acid, decylsulfuric acid, dodecylsulfuric acid, tetradecylsulfuric acid, cetylsulfuric acid, octadecylsulfuric acid, arachylsulfuric acid, and alkali metal salts such as the lithium salt, sodium salt and potassium salt, alkaline earth metal salts such as the magnesium salt and calcium salt, the triethanolammonium salt and the ammonium salt of these acids.

Specific examples of the alkylbenzenesulfonic acid or salt thereof represented by formula (C-2) include hexylbenzenesulfonic acid, octylbenzenesulfonic acid, decylbenzenesulfonic acid, dodecylbenzenesulfonic acid, cetylbenzenesulfonic acid, myristylbenzenesulfonic acid, and alkali metal salts such as the lithium salt, sodium salt and potassium salt, alkaline earth metal salts such as the magnesium salt and calcium salt, the triethanolammonium salt and the ammonium salt of these acids.

Further examples of the anionic surfactant include:
polyoxyethylene alkyl ether sulfuric acids or polyoxyethylene alkyl ether sulfate ester salts represented by general formula (C-3):

$$R^3O(EO)_n(PO)_mSO_3M \quad\quad\quad (C\text{-}3)$$

wherein $R^3$ represents a linear or branched alkyl group of 6 to 30 carbon atoms, M represents a hydrogen atom, an alkali metal atom such as potassium or sodium, an alkaline earth metal atom such as magnesium or calcium, an ammonium ion, or a quaternary ammonium ion, EO represents an ethylene oxide group, PO represents a propylene oxide group, the arrangement of EO and PO may be in blocks or random, and each of n and m independently represents an integer of 0 to 100, provided that n+m>0.

Specific examples include polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene cetyl ether sulfuric acid, polyoxyethylene octadecyl ether sulfuric acid, polyoxyethylene arachyl ether sulfuric acid, and alkali metal salts such as the lithium salt, sodium salt and potassium salt, alkaline earth metal salts such as the magnesium salt and calcium salt, the triethanolammonium salt and the ammonium salt of these acids.

Further examples of the anionic surfactant include:
polyoxyethylene alkylphenyl ether sulfuric acids or polyoxyethylene alkylphenyl ether sulfate ester salts represented by general formula (C-4):

$$R^3\text{—Ph-O}(EO)_n(PO)_mSO_3M \quad\quad\quad (C\text{-}4)$$

wherein $R^3$, M, EO, PO, n and m are as defined in formula (C-3).

Specific examples include polyoxyethylene hexylphenyl ether sulfuric acid, polyoxyethylene octylphenyl ether sulfuric acid, polyoxyethylene decylphenyl ether sulfuric acid, polyoxyethylene dodecylphenyl ether sulfuric acid, polyoxyethylene cetylphenyl ether sulfuric acid, polyoxyethylene myristylphenyl ether sulfuric acid, and alkali metal salts such as the lithium salt, sodium salt and potassium salt, alkaline earth metal salts such as the magnesium salt and calcium salt, the triethanolammonium salt and the ammonium salt of these acids.

Other examples of the component (C) include salts (preferably alkali metal salts or alkaline earth metal salts) of higher fatty acids such as lauric acid, stearic acid, oleic acid and linolenic acid.

The amount used of this component (C) is typically from 1 to 100 parts by mass, preferably from 2 to 25 parts by mass, and particularly preferably from 3 to 10 parts by mass, per 100 parts by mass of the component (A). A single type of the component (C) may be used alone, or a combination of 2 or more types may be used.

Further, the mass ratio between the component (B) and the component (C) is preferably within a range from (B):(C)=1:99 to 65:35. If the value of (B)/(C) exceeds 1.86, then the reaction rate in the emulsion polymerization decreases markedly. If consideration is given to enhancing the stability of the obtained emulsion composition, then (B):(C) is preferably within a range from 20:80 to 55:45, and particularly preferably from 30:70 to 45:55.

<(D) Water>

Water is added in step (I) as component (D-1) in an amount of 1 to 10 parts by mass per 100 parts by mass of the component (A). If an amount of water exceeding 10 parts by mass is added at this point, then obtaining a fine emulsion composition in which the particle size of the emulsion particles is 300 nm or less becomes difficult, whereas if the amount of water is less than 1 part by mass, then obtaining an O/W type emulsion is difficult. The amount of water is preferably from 2 to 8 parts by mass, and particularly preferably from 4 to 6 parts by mass, per 100 parts by mass of the component (A).

Additional water may or may not be added in step (II), but in those cases where water is added as the component (D-2), the amount added is not more than 100,000 parts by mass per 100 parts by mass of the component (A).

<(E) Acid Catalyst>

Provided that the acid catalyst of component (E) is present in the polymerization system during step (II) of the emulsion polymerization, the catalyst may be added at any time. Examples of the acid catalyst include hydrochloric acid, sulfuric acid and a cation exchange resin. However, in those cases where the component (C) has an acid catalytic action, the component (E) need not necessarily be used. Examples of components (C) which act as an acid catalyst include compounds of the aforementioned general formulas (C-1), (C-2), (C-3) and (C-4) in which M represents a hydrogen atom, and specific examples include hexylsulfuric acid, octylsulfuric acid, decylsulfuric acid, dodecylsulfuric acid, tetradecylsulfuric acid, cetylsulfuric acid, octadecylsulfuric acid, arachylsulfuric acid, hexylbenzenesulfonic acid, octylbenzenesulfonic acid, decylbenzenesulfonic acid, dodecylbenzenesulfonic acid, cetylbenzenesulfonic acid, myristylbenzenesulfonic acid, polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene cetyl ether sulfuric acid, polyoxyethylene octadecyl ether sulfuric acid, polyoxyethylene arachyl ether sulfuric acid, polyoxyethylene hexylphenyl ether sulfuric acid, polyoxyethylene octylphenyl ether sulfuric acid, polyoxyethylene decylphenyl ether sulfuric acid, polyoxyethylene dodecylphenyl ether sulfuric acid, polyoxyethylene cetylphenyl ether sulfuric acid and polyoxyethylene myristylphenyl ether sulfuric acid, as well as lauric acid, stearic acid, oleic acid and linolenic acid.

—Step (I)—

The components (A), (B), (C) and (D-1) are emulsified to obtain a first emulsion composition. The emulsification during this step can be performed using an emulsification device such as a homo disper, homo mixer, colloid mill, line mixer, universal mixer, ultra mixer, planetary mixer or combi mix.

In this step, in those cases where the component (C) being used has an acid catalytic action, and those cases where the component (E) is added, condensation also proceeds simultaneously, and therefore it is necessary to perform the emulsification at a temperature of less than 40° C. If the emulsification is performed at a temperature of 40° C. or higher, then there is a concern that the amount of octamethylcyclotetrasiloxane generated may increase. Accordingly, the emulsification is preferably performed at a temperature of less than 15° C., and more preferably performed at a temperature of less than 5° C.

In this step (I), the components (A), (B), (C) and (D-1) are mixed thoroughly until the particle size of the emulsion particles in the first emulsion composition is not more than 300 nm, preferably not more than 200 nm, and particularly preferably 150 nm or less. The smaller the particle size of the emulsion particles of the first emulsion obtained in step (I), the faster the polymerization rate becomes in step (II), meaning the polymerization time can be shortened. Further, as a result of reducing the particle size of the emulsion particles of the first emulsion composition to 300 nm or less, the particle size of the final emulsion particles obtained in the next step is also reduced to 300 nm or less. The particle size of the final emulsion particles is preferably 200 nm or less, and particularly preferably 150 nm or less.

<Step (II)>

At the start of this step, water (D-2) is added in an amount within a range from 0 to 100,000 parts by mass per 100 parts by mass of the component (A), and the resulting emulsion is subjected to emulsion polymerization. In other words, the addition of water prior to the emulsion polymerization is optional, and water need not be added. When water is added, the amount added is not more than 100,000 parts by mass, preferably from 0 to 1,000 parts by mass, and particularly preferably from 0 to 200 parts by mass In those cases where water (D-2) is added to the first emulsion composition in this manner, an emulsification device such as a high-pressure homogenizer may subsequently be used to perform additional emulsification and dispersion.

Next, the emulsion composition is subjected to an emulsion polymerization. This polymerization step is performed at a temperature of less than 40° C. for a period of not more than 48 hours. If the polymerization is performed at a temperature of 40° C. or higher, then there is a concern that the amount of octamethylcyclotetrasiloxane generated may increase. Accordingly, the polymerization is preferably performed at a temperature of less than 15° C., and more preferably performed at a temperature of less than 5° C. Further, if the polymerization time exceeds 48 hours, then there is a concern that the amount of octamethylcyclotetrasiloxane generated may increase. Accordingly, the polymerization time is preferably within a range from 1 to 30 hours, and particularly preferably from 5 to 24 hours.

The viscosity of the organopolysiloxane produced in the emulsion polymerization is at least 300,000 mPa·s, preferably 1,000,000 mPa·s or greater, and particularly preferably 5,000,000 mPa·s or greater. Further, the octamethylcyclotetrasiloxane content within the organopolysiloxane produced in the emulsion polymerization is not more than 3,000 ppm, preferably not more than 2,000 ppm, and particularly preferably 1,000 ppm or less.

By performing the emulsion polymerization in the presence of the acid catalyst (E), the polymerization is accelerated, and the polymerization time can be shortened. When the anionic surfactant of the component (C) has an acid catalyst function, a separate acid catalyst (E) may or may not be added to the polymerization system in addition to the component (C).

According to the method for producing an emulsion composition of the present invention, the viscosity (25° C.) of the produced organopolysiloxane reaches at least 300,000 mPa·s in a polymerization time of not more than 15 hours, and typically in a time within a range from 5 to 15 hours. The viscosity reached within 15 hours is preferably 500,000 mPa·s or greater, more preferably 1,000,000 mPa·s or greater, and particularly preferably 5,000,000 mPa·s or greater.

<Other Processing>

Following completion of the polymerization, the obtained emulsion composition is usually neutralized with a basic substance. Examples of the basic substance include sodium hydroxide, potassium hydroxide, sodium hydrogen carbonate, and amine compounds such as triethanolamine and triethylamine.

Water may be added at this time to adjust the silicone concentration, and a preservative or antifungal agent or the like may be added to improve the storage properties of the emulsion composition.

By adding an organopolysiloxane such as $R^1_3SiO(R^1_2SiO)_nSiR^1_3$ to the emulsion composition obtained following the step (I) of performing emulsification and the step (II) of conducting emulsion polymerization, or following completion of the subsequent neutralization, an organopolysiloxane in which the terminals are blocked with unreactive triorganosiloxy groups can be obtained, whereas by adding an alkoxysilane such as $R^1_3Si(OR^4)_1$, $R^1_2Si(OR^4)_2$ or $R^1_1Si(OR^4)_3$ to the emulsion composition, branched units can be introduced into the obtained organopolysiloxane chain, and a variety of functional groups can also be introduced. Here, $R^1$ is as defined above, and represents a hydrogen atom or a substituted or unsubstituted hydrocarbon group of 1 to 20 carbon atoms, and preferably 1 to 6 carbon atoms. Specific examples of $R^1$ include a methyl group, ethyl group, propyl group, butyl group and phenyl group. $R^4$ represents identical or different alkyl groups of 1 to 20 carbon atoms or a hydrogen atom. Moreover, n represents an integer of 0 to 100.

EXAMPLES

In the following description of examples and comparative examples, "parts" means "parts by mass".

The properties described below of the emulsion compositions obtained in the various examples were measured or evaluated in the manner described below.

Average Particle Size in Emulsion:

The value for the median particle size measured using a laser diffraction and scattering particle size distribution measurement apparatus LA-920 (manufactured by Horiba, Ltd.).

Viscosity of Organopolysiloxane:

The viscosity at 25° C., obtained by adding 300 g of isopropyl alcohol to 300 g of the prepared emulsion composition with constant stirring, collecting only the precipitated dimethylsiloxane, drying the dimethylsiloxane at 105° C. for 3 hours, and then measuring the viscosity at 25° C. using a rotational viscometer.

Octamethylcyclotetrasiloxane Content of Organopolysiloxane:

A 0.1 g sample of the prepared emulsion composition was extracted (shaken for 3 hours) with 10 ml of acetone containing 20 ppm of tetradecane as an internal standard, and following standing overnight, the acetone layer was collected and analyzed by gas chromatography to quantify the amount of octamethylcyclotetrasiloxane.

Emulsion Stability:

The prepared emulsion composition was placed in a 100 ml glass bottle, and following storage at 50° C. for one month, the external appearance of the emulsion was inspected. If the emulsion formed a uniform single phase and no separation was noticeable, the stability was evaluated as good and was recorded using the symbol "O", whereas if the emulsion had separated into two phases, the stability was evaluated as poor and was recorded using the symbol "x".

Example 1

To 100 parts by mass of an organopolysiloxane having silanol groups at the molecular chain terminals and having a viscosity of 5,000 mm$^2$/s (a compound of general formula (1) in which $R^1$=a methyl group, and the octamethylcyclotetrasiloxane content is 50 ppm or less) were added 3.0 parts by mass of a polyoxyalkylene (10 mol) branched decyl ether, 4.0 parts by mass of dodecylbenzenesulfonic acid and 6.0 parts by mass of water, and the resulting mixture was emulsified using a homo disper. Separate samples of the thus obtained first emulsion were subjected to emulsion polymerization at 0° C. for 15 hours and 20 hours respectively. Subsequently, 2.4 parts by mass of triethanolamine and 84.6 parts by mass of water were added to the obtained emulsion, and dilution and dispersion were performed using a homo mixer to obtain the target emulsion composition. The results are as shown in Table 1.

Example 2

To 100 parts by mass of an organopolysiloxane having silanol groups at the molecular chain terminals and having a viscosity of 5,000 mm$^2$/s (a compound of general, formula (1) in which $R^1$=a methyl group, and the octamethylcyclotetrasiloxane content is 50 ppm or less) were added 3.0 parts by mass of a polyoxyalkylene (10 mol) branched decyl ether, 4.0 parts by mass of dodecylbenzenesulfonic acid and 6.0 parts by mass of water, and the resulting mixture was emulsified using a homo disper. To the thus obtained first emulsion was added 84.6 parts by mass of water, and dilution and dispersion were performed using a homo mixer. Separate samples of the thus obtained emulsion were subjected to emulsion polymerization at 0° C. for 10 hours and 15 hours respectively. Subsequently, the obtained emulsion was neutralized by adding 2.4 parts by mass of triethanolamine, thus obtaining the target emulsion composition. The results are as shown in Table 1.

Example 3

To 100 parts by mass of an organopolysiloxane having silanol groups at the molecular chain terminals and having a viscosity of 5,000 mm$^2$/s (a compound of general formula (1) in which $R^1$=a methyl group, and the octamethylcyclotetrasiloxane content is 50 ppm or less) were added 6.0 parts by mass of a polyoxyalkylene (10 mol) branched decyl ether, 8.0 parts by mass of dodecylbenzenesulfonic acid and 6.0 parts by mass of water, and the resulting mixture was emulsified using a homo disper. Separate samples of the thus obtained first emulsion were subjected to emulsion polymerization at 0° C. for 15 hours and 20 hours respectively. Subsequently, 4.8 parts by mass of triethanolamine and 125.2 parts by mass of water were added to the obtained emulsion, and dilution and dispersion were performed using a homo mixer to obtain the target emulsion composition. The results are as shown in Table 1.

Example 4

To 100 parts by mass of an organopolysiloxane having silanol groups at the molecular chain terminals and having a viscosity of 5,000 mm$^2$/s (a compound of general formula (1) in which $R^1$=a methyl group, and the octamethylcyclotetrasiloxane content is 50 ppm or less) were added 6.0 parts by mass of a polyoxyalkylene (10 mol) branched decyl ether, 8.0 parts of dodecylbenzenesulfonic acid and 6.0 parts of water, and the resulting mixture was emulsified using a homo disper. To the thus obtained first emulsion was added 125.2 parts by mass of water, and dilution and dispersion were performed using a homo mixer. Separate samples of the thus obtained emulsion were subjected to emulsion polymerization at 0° C. for 15 hours and 20 hours respectively. Subsequently, the obtained emulsion was neutralized by adding 4.8 parts by mass of triethanolamine, thus obtaining the target emulsion composition. The results are as shown in Table 1.

Example 5

To 100 parts by mass of an organopolysiloxane having silanol groups at the molecular chain terminals and having a viscosity of 5,000 mm$^2$/s (a compound of general formula (1) in which $R^1$=a methyl group, and the octamethylcyclotetrasiloxane content is 50 ppm or less) were added 4.0 parts by mass of a polyoxyalkylene (10 mol) branched decyl ether, 4.0 parts of dodecylbenzenesulfonic acid and 6.0 parts of water, and the resulting mixture was emulsified using a homo disper. To the thus obtained first emulsion was added 83.6 parts by mass of water, and following dilution and dispersion using a homo mixer, separate samples of the emulsion were subjected to emulsion polymerization at 0° C. for 15 hours and 20 hours respectively. Subsequently, neutralization was performed with 2.4 parts by mass of triethanolamine to obtain an emulsion composition. The results are as shown in Table 1.

Comparative Example 1

To 100 parts by mass of an organopolysiloxane having silanol groups at the molecular chain terminals and having a viscosity of 5,000 mm$^2$/s (a compound of general formula (1) in which $R^1$=a methyl group, and the octamethylcyclotetrasiloxane content is 50 ppm or less) were added 3.0 parts by mass of a polyoxyalkylene (10 mol) branched decyl ether, 4.0 parts by mass of dodecylbenzenesulfonic acid and 11.88 parts by mass of water, and the resulting mixture was emulsified using a homo disper to obtain a first emulsion. Separate samples of the emulsion were subjected to emulsion polymerization at 0° C. for 15 hours and 20 hours respectively. Subsequently, 2,4 parts by mass of triethanolamine and 78.72 parts by mass of water were added, and dilution and dispersion were performed using a homo mixer to obtain an emulsion composition. The results are as shown in Table 1.

As is evident from the results in Table 1, in this comparative example, because a large amount of water (11.88 parts by mass) was used during preparation of the first emulsion, the average particle size of the emulsion particles was not reduced to 300 rim or less. Further, because the particle size was larger, the viscosity only increased to 590,000 mPa·s even when the emulsion polymerization was performed for 20 hours.

Comparative Example 2

To 100 parts by mass of an organopolysiloxane having silanol groups at the molecular chain terminals and having a viscosity of 60 mm$^2$/s (a compound of general formula (1) in which R$^1$=a methyl group, and the octamethylcyclotetrasiloxane content is 260 ppm) were added 10 parts by mass of 10% sodium lauryl sulfate and 10 parts by mass of water, and the resulting mixture was emulsified uniformly using a homo mixer. An additional 74 parts by mass of water was added to the thus obtained first emulsion, and the mixture was emulsified and dispersed 3 times using a high-pressure homogenizer at a pressure of 50 MPa. Subsequently, 5.0 parts by mass of 10% dodecylbenzenesulfonic acid was added to the emulsion, and the mixture was subjected to an emulsion polymerization at 0° C. for 20 hours. Following the polymerization, 1.0 parts by mass of a 10% aqueous solution of sodium carbonate was added to neutralize the mixture and obtain an emulsion composition. The results are as shown in Table 1.

However, it is evident that because the emulsion composition obtained in this manner used an organopolysiloxane having silanol groups at the molecular chain terminals and having a low viscosity as the raw material, even when the emulsion polymerization was conducted for 20 hours, the viscosity of the dimethylpolysiloxane in the emulsion composition only increased to 550,000 mPa·s, and the octamethylcyclotetrasiloxane content could not be suppressed to 3,000 ppm or less.

Comparative Example 3

To 100 parts of an organopolysiloxane having silanol groups at the molecular chain terminals and having a viscosity of 60 nun$^2$/s (a compound of general formula (1) in which R$^1$=a methyl group, and the octamethylcyclotetrasiloxane content is 260 ppm) were added 5.0 parts by mass of polyoxyethylene (9 mol) lauryl ether, 5.0 parts by mass of dodecylbenzenesulfonic acid and 12.5 parts by mass of water, and the resulting mixture was emulsified uniformly using a homo mixer to obtain a first emulsion. An additional 127.5 parts by mass of water was added to the emulsion, and the mixture was emulsified and dispersed 3 times using a high-pressure homogenizer at a pressure of 50 MPa. Subsequently, the mixture was subjected to an emulsion polymerization at 25° C. for 20 hours. Next, 10 parts by mass of a 10% aqueous solution of sodium carbonate was added to neutralize the mixture and obtain an emulsion composition. The results are as shown in Table 1.

However, it is evident that because the emulsion composition obtained in this manner used an organopolysiloxane having silanol groups at the molecular chain terminals and having a low viscosity as the raw material, even when the emulsion polymerization was conducted for 20 hours, the siloxane viscosity in the emulsion only increased to 320,000 mPa·s, and the octamethylcyclotetrasiloxane content could not be suppressed to 3,000 ppm or less.

Comparative Example 4

To 100 parts by mass of an organopolysiloxane having silanol groups at the molecular chain terminals and having a viscosity of 5,000 mm$^2$/s (a compound of general formula (1) in which R$^1$=a methyl group, and the octamethylcyclotetrasiloxane content is 50 ppm or less) were added 4.0 parts by mass of a polyoxyalkylene (10 mol) branched decyl ether, 2.0 parts of dodecylbenzenesulfonic acid and 6.0 parts of water, and the resulting mixture was emulsified using a homo disper. To the thus obtained first emulsion was added 86.8 parts by mass of water, and following dilution and dispersion using a homo mixer, the emulsion was subjected to emulsion polymerization at 0° C. for 20 hours. Following the polymerization, the emulsion was neutralized by adding 1.2 parts by mass of triethanolamine, thus obtaining an emulsion composition. The results are as shown in Table 1.

However, in this comparative example, because the ratio of nonionic surfactant (B):anionic surfactant (C)=66:34, the polymerization was inhibited, and it is evident that even when the emulsion polymerization was conducted for 20 hours, the viscosity of the dimethylpolysiloxane in the obtained emulsion only increased to 300,000 mPa·s.

TABLE 1

|  | Water amount (parts by mass) | Polymerization time (hours) | Nonionic surfactant: Anionic surfactant | Average particle size (nm) | Viscosity (mPa·s) | D$_4$ content (ppm) | Stability (50° C., 1 month) |
|---|---|---|---|---|---|---|---|
| Example 1 | 6 | 15 | 43:57 | 160 | 7,400,000 | 1000 | ○ |
|  | 6 | 20 | 43:57 | 160 | 19,000,000 | 1300 | ○ |
| Example 2 | 6 | 10 | 43:57 | 180 | 700,000 | 1000 | ○ |
|  | 6 | 15 | 43:57 | 170 | 8,800,000 | 1400 | ○ |
| Example 3 | 6 | 15 | 43:57 | 140 | 4,700,000 | 980 | ○ |
|  | 6 | 20 | 43:57 | 140 | 12,000,000 | 1200 | ○ |
| Example 4 | 6 | 15 | 43:57 | 140 | 6,800,000 | 1400 | ○ |
|  | 6 | 20 | 43:57 | 130 | 16,000,000 | 1800 | ○ |
| Example 5 | 6 | 15 | 50:50 | 150 | 2,200,000 | 1200 | ○ |
|  | 6 | 20 | 50:50 | 150 | 5,200,000 | 1500 | ○ |
| Comparative Example 1 | 11.88 | 15 | 43:57 | 560 | 100,000 | 730 | x |
|  | 11.88 | 20 | 43:57 | 530 | 590,000 | 950 | x |
| Comparative Example 2 | 10 | 20 | 0:100 | 320 | 550,000 | 18300 | ○ |

TABLE 1-continued

| | Water amount (parts by mass) | Polymerization time (hours) | Nonionic surfactant: Anionic surfactant | Average particle size (nm) | Viscosity (mPa·s) | D₄ content (ppm) | Stability (50° C., 1 month) |
|---|---|---|---|---|---|---|---|
| Comparative Example 3 | 12.5 | 20 | 50:50 | 270 | 320,000 | 28300 | ○ |
| Comparative Example 4 | 6 | 20 | 66:34 | 200 | 300,000 | — | ○ |

(Notes)
D₄: octamethylcyclotetrasiloxane
Water amount: the amount of water added per 100 parts by mass of the raw material organopolysiloxane in step (I).

INDUSTRIAL APPLICABILITY

The composition of the present invention has excellent stability and exhibits an excellent sensation during use, and is therefore particularly useful as a cosmetic material or an item for household use. For example, the invention can be used in hair care products such as shampoos and rinses. Further, the invention can also be used as a protective material for furniture and miscellaneous goods, as a release agent for molds used in processing rubber products or plastic products, or as a fiber treatment agent used for imparting water repellency or flexibility to fibers.

The invention claimed is:

1. A method for producing an organopolysiloxane emulsion composition, the method comprising:
   (I) preparing a first emulsion composition by performing emulsification of a mixture comprising:
      (A) 100 parts by mass of an organopolysiloxane represented by general formula (1) shown below, and having an octamethylcyclotetrasiloxane content of not more than 1,000 ppm, $$HO(R^1_2SiO)_nH \quad (1)$$

wherein each $R^1$ independently represents a hydrogen atom or a substituted or unsubstituted hydrocarbon group of 1 to 20 carbon atoms, and n represents a number that yields a viscosity at 25° C. for the organopolysiloxane of 3,000 to 100,000 mm²/s,
      (B) 1 to 100 parts by mass of a nonionic surfactant,
      (C) 1 to 100 parts by mass of an anionic surfactant,
      provided that a mass ratio of component (B):component (C) is within a range from 20:80 to 55:45, and
      (D-1) 1 to 10 parts by mass of water; and
   (II) subjecting the first emulsion composition to emulsion polymerization,
      either without adding any water, or following addition of (D-2) not more than 100,000 parts by mass of water,
      the emulsion polymerization performed at a temperature of less than 40° C., in presence of an acid catalyst (E) (although the acid catalyst is unnecessary in those cases where the anionic surfactant (C) has a catalytic action),
      thus preparing a target emulsion composition, in which a viscosity at 25° C. of the organopolysiloxane generated in a polymerization time of not more than 15 hours is 300,000 mPa·s or greater, and an amount of octamethylcyclotetrasiloxane contained in the organopolysiloxane is not more than 3,000 ppm.

2. The method for producing an organopolysiloxane emulsion composition according to claim 1, wherein an average particle size of emulsion particles in the obtained target emulsion composition is 300 nm or less.

3. The method for producing an organopolysiloxane emulsion composition according to claim 1, wherein a viscosity at 25° C. of the organopolysiloxane in the obtained target emulsion composition is 1,000,000 mPa·s or greater.

4. The method for producing an organopolysiloxane emulsion composition according to claim 2, wherein a viscosity at 25° C. of the organopolysiloxane in the obtained target emulsion composition is 1,000,000 mPa·s or greater.

5. The method for producing an organopolysiloxane emulsion composition according to claim 1, wherein a mass ratio of component (B) : component (C) is within a range from 30:70 to 45:55.

* * * * *